(12) United States Patent
Shen et al.

(10) Patent No.: US 8,720,288 B2
(45) Date of Patent: May 13, 2014

(54) COUNTER ASSEMBLY, SHEATH FLOW IMPEDANCE COUNT DEVICE, AND FLOW CYTOMETER ANALYZER

(75) Inventors: Tao Shen, Shenzhen (CN); Wenheng Guo, Shenzhen (CN); Jin Teng, Shenzhen (CN)

(73) Assignee: Shenzhen Mindray Bio-Medical Electronics Co., Ltd, Shenzhen (CN)

( * ) Notice: Subject to any disclaimer, the term of this patent is extended or adjusted under 35 U.S.C. 154(b) by 385 days.

(21) Appl. No.: 13/335,763

(22) Filed: Dec. 22, 2011

(65) Prior Publication Data

US 2012/0160017 A1    Jun. 28, 2012

(30) Foreign Application Priority Data

Dec. 28, 2010   (CN) .......................... 2010 1 0609840

(51) Int. Cl.
*G01N 27/00*    (2006.01)
(52) U.S. Cl.
USPC ....................................... 73/865.5

(58) Field of Classification Search
None
See application file for complete search history.

(56) References Cited

U.S. PATENT DOCUMENTS

| | | | |
|---|---|---|---|
| 4,972,137 A | 11/1990 | Dunstan et al. | |
| 5,905,214 A | 5/1999 | Inami | |
| 6,417,658 B1 | 7/2002 | Inami | |
| 6,909,269 B2 | 6/2005 | Nagai et al. | |
| 7,658,121 B2 * | 2/2010 | Zhao et al. ................. | 73/864.22 |

FOREIGN PATENT DOCUMENTS

| CN | 1044284 C | 7/1999 |
|---|---|---|
| CN | 101173887 B | 4/2011 |

\* cited by examiner

*Primary Examiner* — Robert R Raevis
(74) *Attorney, Agent, or Firm* — Kory D. Christensen; Stoel Rives LLP

(57) ABSTRACT

A counter assembly, sheath flow impedance count device, and flow cytometer analyzer are disclosed.

10 Claims, 4 Drawing Sheets

COUNTER ASSEMBLY, SHEATH FLOW IMPEDANCE COUNT DEVICE, AND FLOW CYTOMETER ANALYZER

CROSS-REFERENCE TO RELATED APPLICATIONS

This application claims the benefit of Chinese Patent Application No. 201010609840.X, filed Dec. 28, 2010, which is incorporated herein by reference in its entirety.

TECHNICAL FIELD

The following disclosure relates to blood analyzers.

SUMMARY OF THE INVENTION

Disclosed herein are embodiments of a counter assembly, sheath flow impedance count device, and flow cytometer analyzer.

DETAILED DESCRIPTION

Figure 1:
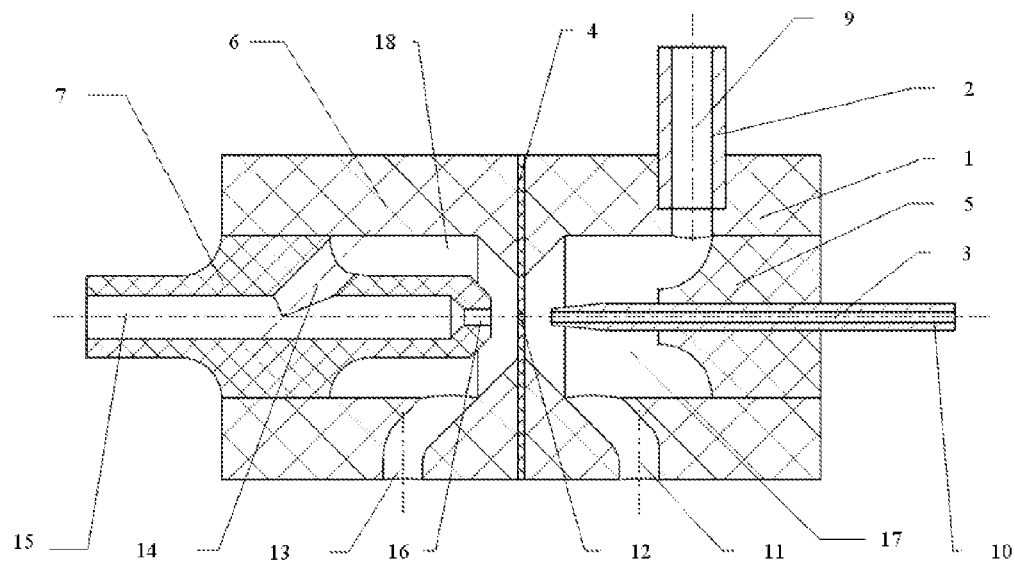
FIG. 1 is a vertical cross-sectional view of a counter.
Figure 2:
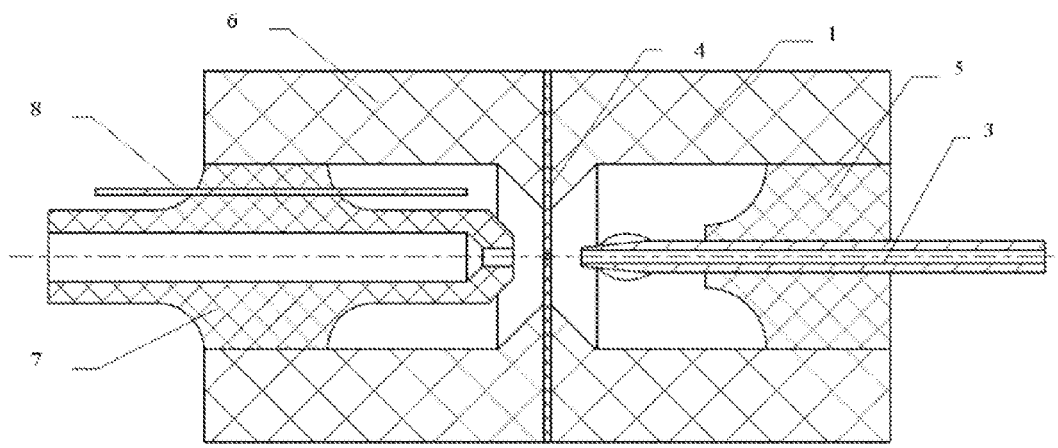
FIG. 2 is a horizontal cross-sectional view of a counter.

Sheath flow impedance counting is commonly used in blood analyzers. A counter assembly is shown in FIGS. 1 and 2. The counter assembly includes a front chamber housing 1, a negative electrode 2, a sample needle 3, a partition plate 4, a sample needle pedestal 5, a rear chamber housing 6, a capture tube 7, and a positive electrode 8. The front chamber housing 1 defines a front cell 17, and the front chamber housing 1 includes a front sheath liquid inlet 9, a sample liquid inlet 10, and a front cell washing inlet 11, which are all in communication with the front cell 17. The rear chamber housing 6 defines a rear cell 18. The rear chamber housing 6 includes a rear sheath liquid inlet 13 in communication with the rear cell 18. The capture tube 7 is disposed inside the rear cell 18. The capture tube 7 includes a capture tube inlet 16, a rear washing outlet 14, and a waste liquid outlet 15. The partition plate 4 isolates the front chamber housing 1 and the rear chamber housing 6. The partition plate 4 has a counting hole 12 in the middle through which the front cell 17 communicates with the rear cell 18.

When counting, the front sheath liquid flows into the front cell 17 through the front sheath liquid inlet 9, and the rear sheath liquid flows into the rear cell 18 through the rear sheath liquid inlet 13. The sample liquid containing particles flows into the front cell 17 through the sample liquid inlet 10, and then flows into the rear cell 18 through the counting hole 12 embraced by the front sheath liquid, into the capture tube 7 through the capture tube inlet 16 embraced by the rear sheath liquid, and out through the waste liquid outlet 15.

During the counting process, a constant current source is applied between the negative electrode 2 and the positive electrode 8 to form a constant electrical field with a constant voltage between the front cell 17 and the rear cell 18. Particles and reagents differ in electrical conductivity; that is, the particles are less conductive than the reagents. Therefore, when the particles pass through the counting hole 12, the voltage drop between the negative electrode 2 and the positive electrode 8 is increased. The voltage drop becomes greater as the size of the particle increases. Thus, the size of a particle can be measured according to a voltage drop variation. A total amount of the particles can be measured according to the number of times varying voltage drop variation is detected, and a concentration of the sample liquid can be measured after measuring a volume of the sample liquid. The above described method is referred to as a sheath flow impedance count method.

Due to the influence of the electrical field and other factors, including pressure, the reagents release gases slowly in the front cell 17 and rear cell 18. The gases can accumulate to form a large bubble, which interferes with the electrical field between the front cell 17, the rear cell 18, and the counting hole 12. This can result in an incorrect particle count. Therefore, it is beneficial to eliminate the bubbles in the front and rear cells 17, 18 after the counter has been in operation for a period of time.

In order to discharge the bubbles in the front cell 17, a washing liquid flows in from the front cell washing inlet 11 and out from the front sheath liquid inlet 9. In order to discharge the bubbles in the rear cell 18, the reagents flow in from the rear sheath liquid inlet 13 and out from the rear washing outlet 14, and eventually out from the waste liquid outlet 15 taking away the possible bubbles.

When applying the sheath flow impedance count method, because the front and rear cells 17, 18 receive fluid from the same source, in order to ensure that the electrical connection between the front and rear sheath liquids is not short-circuited, the front and rear sheath liquids need to be isolated. In other words, the front cell 17 and the rear cell 18 have no other electrical connection except the counting hole 12.

A problem arises, however, because, on one hand, the rear sheath and the front sheath need to have no actual connection, on the other hand, the rear sheath needs to be continuous. Currently, most counters employ a "dripping-in" method; that is, liquid drips into the rear sheath liquid inlet and drips out of the outlet.

Figure 3:
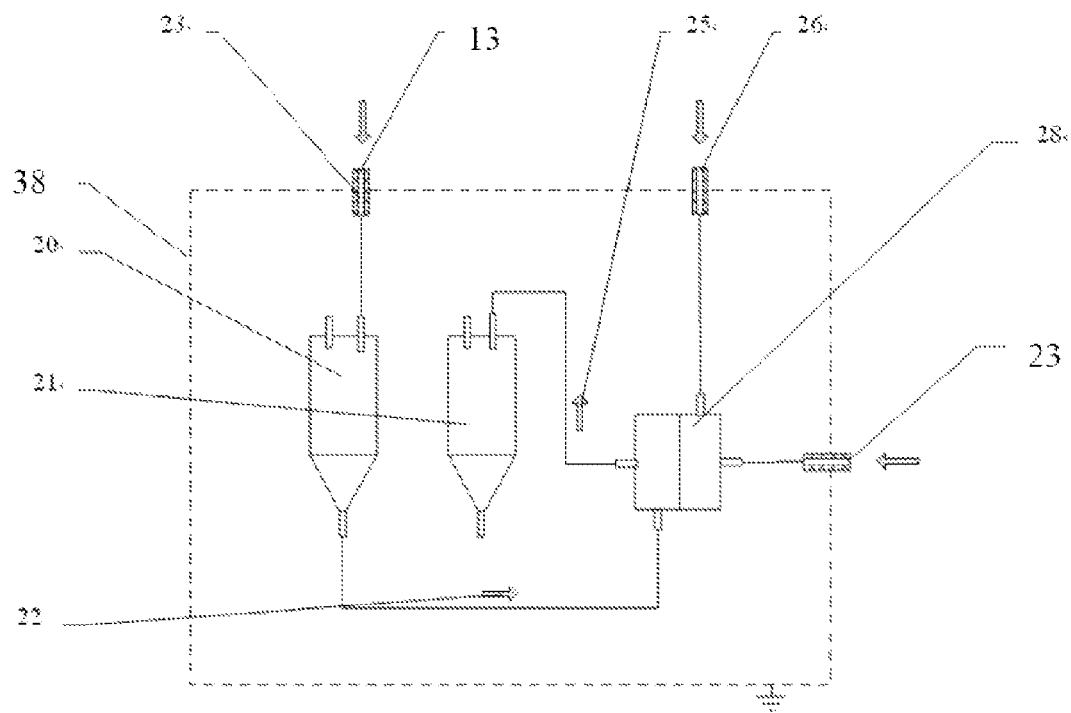
FIG. 3 is a schematic diagram of a typical count device.

FIG. 3 shows a basic structure view of a typical counting device. A shielding box 38 prevents outside electromagnetic signals from disturbing the measuring signals. The shielding box 38 has multiple shielding connectors 23 through which to ensure that liquid flowing therein is directly short connected with the shielding box. The rear sheath isolation chamber 20 isolates the rear cell and the rear sheath liquid dripping-in tube. The waste liquid isolation chamber 21 isolates the rear cell and the waste liquid discharging tube.

When counting, the rear sheath liquid flows into the rear sheath isolation chamber 20 from the rear sheath liquid inlet 13 using the dripping technique, after which it flows into the counter 28 along the rear sheath flow 22. The waste liquid flows along the waste flow 25 to the waste liquid isolation chamber 21. Therefore, the rear cell of the counter 28 has no connection except the counting hole 12.

Because bubbles can disturb the flow field and the electrical field, bubbles should be prevented from entering the counter. Accordingly, the liquid surface of the sheath liquid of the rear sheath isolation chamber should be properly configured. Too high of a surface may lose the isolation effect; too low of a surface may cause bubbles to enter into the counter along the tube.

There are two solutions to control the rear sheath isolation chamber 20:

1. adding a surface sensor in the rear sheath isolation chamber 20; and
2. sealing the rear sheath isolation chamber 20.

As for solution 1, adding a sensor may cause electromagnetic interference and may also lead to a complicated structure.

As for solution 2, the same volume of the liquid should theoretically be flowing out and for the liquid surface to be kept constant. However, there are two problems. One relates to how to ensure that the liquid surface is an acceptable height when the counter begins working. The other one is that, due to variations of the pressure and temperature, as well as dripping action, gases escape from or dissolve in the liquid, which further causes the liquid surface to change and even lose control during continuous, long-term operation.

This disclosure provides a counter assembly, sheath flow impedance count device, and flow cytometer analyzer, in which stability of the liquid surface in the rear sheath isolation chamber is improved.

According to one embodiment, a counter assembly includes a counter, a waste liquid isolation chamber, a rear sheath isolation chamber, and a pressure balance tube. The counter has a front cell, a rear cell, a rear sheath liquid inlet, and a waste liquid outlet, and the front cell and rear cell communicate through a counting hole. The rear sheath liquid inlet and the waste liquid outlet are in communication with the rear cell. The rear sheath isolation chamber and the rear sheath liquid inlet are connected with each other, and the waste liquid isolation chamber is connected with the waste liquid outlet. The pressure balance tube is connected to the rear sheath isolation chamber and the waste liquid isolation chamber, and the pressure balance tube has a pressure balance controller providing an on/off control.

In one embodiment, the rear sheath isolation chamber includes a first cell and a first liquid adding inlet, and the first liquid adding inlet extends downwardly into the inside of the first cell. The waste liquid isolation chamber includes a second cell and a second liquid adding inlet, and the second liquid adding inlet extends downwardly into the inside of the second cell. A bottom of the first liquid adding inlet is higher than a bottom of the second liquid adding inlet. Using a siphoning process, the rear sheath isolation chamber has a faster and more convenient initialization operation.

In various embodiments, a bottom of the first cell is higher than a bottom of the second cell. The rear sheath isolation chamber is in communication with the atmosphere through a gas tube.

The rear sheath isolation chamber may have an oblique guiding surface, by which the possibility of bringing gas into the liquid when adding liquid can be reduced. The first liquid adding inlet may be disposed obliquely. The guiding surface may be a side surface of the first liquid adding inlet.

In one embodiment, the rear sheath isolation chamber further includes a first top cover disposed at the top of the first cell. The first liquid adding inlet is disposed above the first top cover. The first top cover has a first connector. The waste liquid isolation chamber further includes a second top cover disposed at the top of the second cell. The second liquid adding inlet is disposed above the second top cover. The second top cover has a second connector. The bottom of the first cell is connected with the rear sheath liquid inlet. The pressure balance tube is connected with the first connector and the second connector.

According to one embodiment, a sheath flow impedance count device includes a counter assembly, a rear sheath adding tube, a front sheath adding tube, a rear sheath waste liquid discharging tube, and a front sheath waste liquid discharging tube. The front sheath adding tube and the front sheath waste liquid discharging tube are connected to the front cell of the counter assembly. The rear sheath isolation chamber is connected to the rear sheath adding tube and the rear cell of the counter assembly. The rear sheath waste liquid discharging tube is connected to the rear cell of the counter assembly.

In one embodiment, the sheath flow impedance count device further includes a first container and a second container. The front sheath adding tube and the rear sheath adding tube are connected to the first container. The front sheath waste liquid discharging tube and the rear sheath waste liquid discharging tube are connected to the second container. The first container has a positive pressure, and the second container has a negative pressure.

In one embodiment, the device further includes a shielding box. The counter assembly is located inside the shielding box. At least one of the rear sheath adding tube, the front sheath adding tube, the rear sheath waste liquid discharging tube, and the front sheath waste liquid discharging tube has an internal tube inside the shielding box and an external tube outside the shielding box. The internal tube and the external tube are connected to each other through a shielding connector.

During a washing and counting process, the pressure balance controller can control whether the pressure balance tube is turned on or off. The rear sheath isolation chamber has a sealed space above the liquid surface therein, such that the volume flowing out is the same as the volume flowing in, improving the stability of the liquid surface. During a process of discharging the waste liquid isolation chamber, the pressure balance controller is turned on, and the waste liquid isolation chamber and the rear sheath isolation chamber are connected and have the same pressure, which improves the stability of the liquid surface of the rear sheath isolation chamber.

Figure 4:
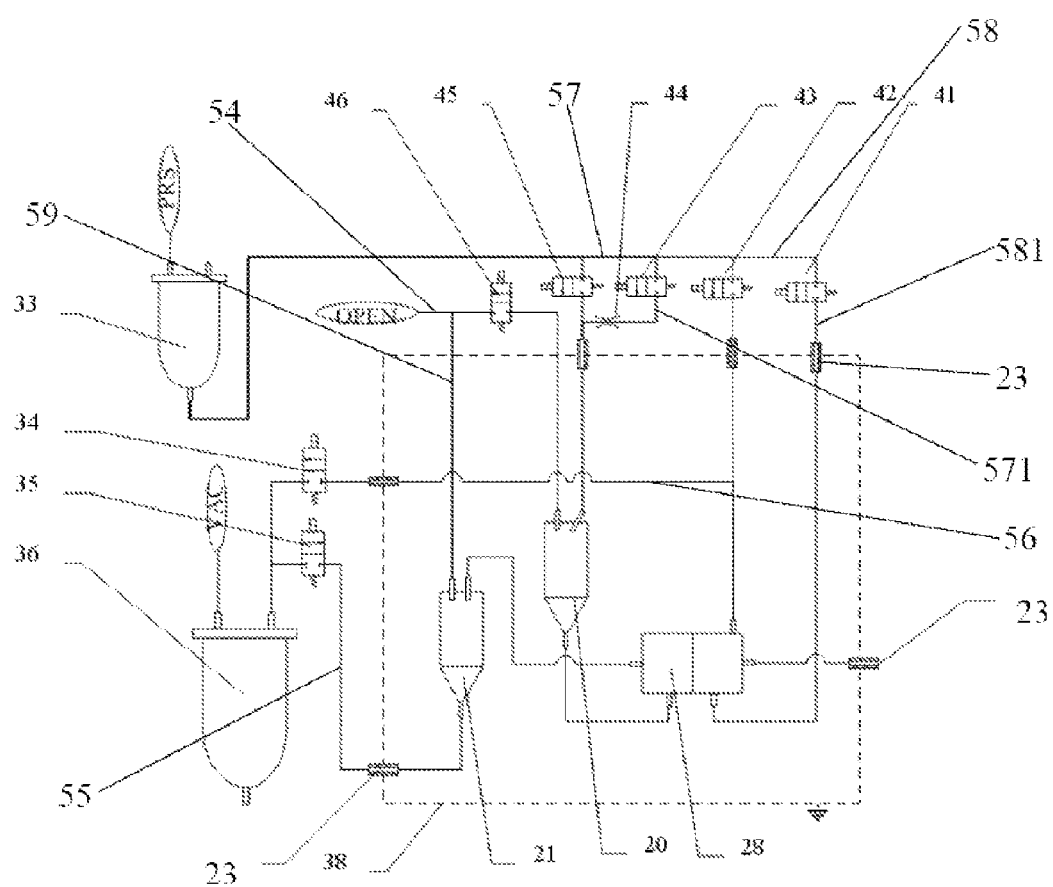
FIG. 4 is a schematic diagram of a sheath flow count device.
Figure 5:
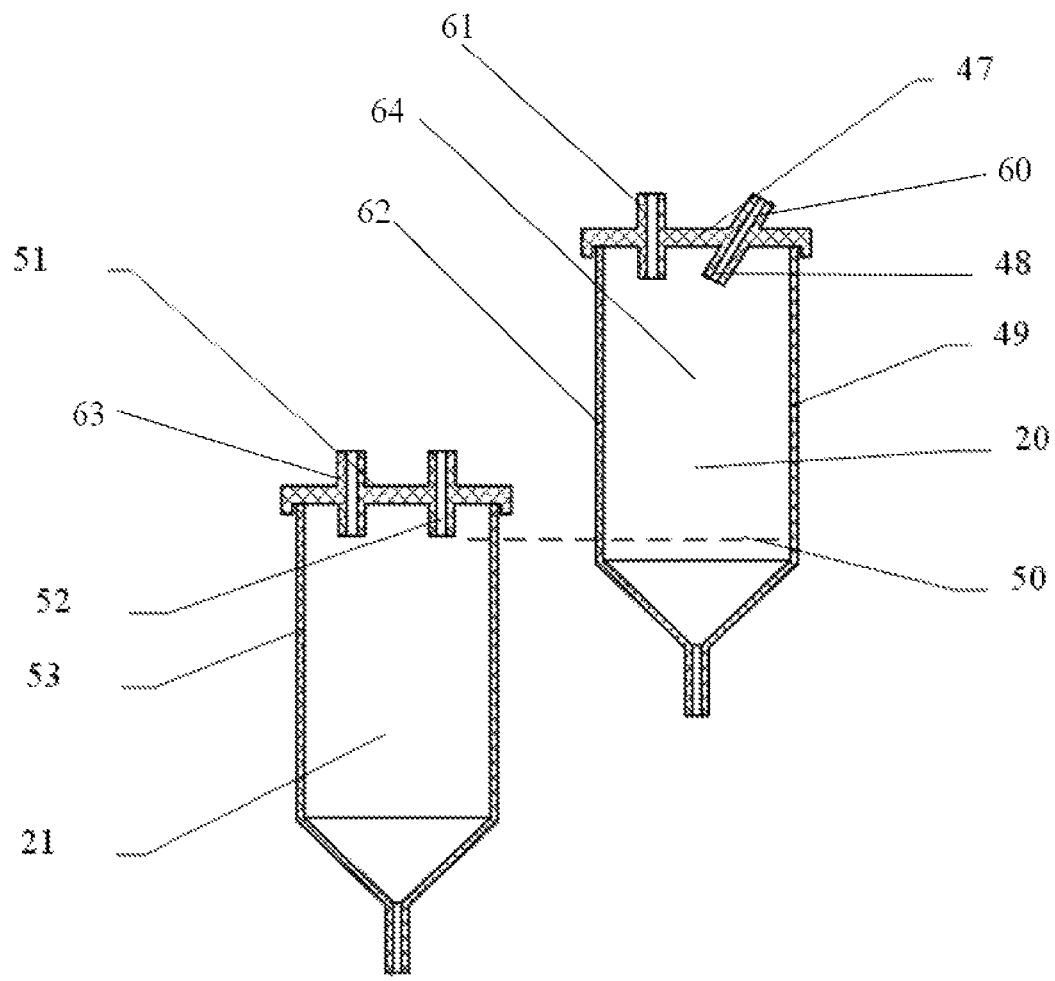
FIG. 5 is a schematic diagram showing a relative position of a waste liquid isolation chamber and a rear sheath isolation chamber of a sheath flow count device.

As shown in FIGS. 1, 4, and 5, one embodiment of a sheath flow impedance count device includes a counter assembly, a first container 33, and a second container 36. The counter assembly includes a counter 28, a rear sheath isolation chamber 20, and a waste liquid isolation chamber 21. The counter 28 has a front cell 17, a front cell washing inlet 11, a front sheath liquid inlet 9, and a sample liquid inlet 10. The front washing inlet 11, front sheath liquid inlet 9, and sample liquid inlet 10 are in communication with the front cell 17. The counter further includes a rear cell 18, a rear sheath liquid inlet 13, and a waste liquid outlet 15. The rear sheath liquid inlet 13 and the waste liquid inlet 15 are in communication with the rear cell 18. A partition plate 4 may be disposed between the front cell 17 and the rear cell 18, and the partition plate 4 may have a counting hole 12 in communication with the front cell 17 and the rear cell 18.

The rear sheath isolation chamber 20 is used for isolating the rear sheath liquid adding tube 57 and the rear cell 18. The waste liquid isolation chamber 21 is used for isolating the rear sheath waste liquid discharging tube 55 and the rear cell 18. The waste liquid isolation chamber 21 is in communication with the atmosphere through a gas tube 54. The first container 33 is used for storing sheath liquid for the counting process and washing liquid for the washing process.

The first container 33 may have a positive pressure. The positive pressure can be used to drive the flow of the sheath liquid and washing liquid. In one embodiment, the first container 33 is connected to the rear sheath isolation chamber 20 through the rear sheath liquid adding tube 57. The first container 33 further is connected to the front cell 17 through the front sheath liquid adding tube 58. The second container 36 is used for containing waste liquid, which may have a negative pressure. The negative pressure can be used to drive the flow of waste liquid.

The second container 36 is connected to the waste liquid isolation chamber 21 through the rear sheath waste liquid discharging tube 55. The second container 36 may also be connected to the front cell 17 through the front sheath waste liquid discharging tube 56. The rear sheath waste liquid discharging tube 55 may have a waste liquid isolation chamber controller 35 to control whether the tube is on or off. The front sheath waste liquid discharging tube 56 may have a front cell waste controller 34 to control whether the tube is on or off.

In one embodiment, the front sheath liquid adding tube 58 includes two first branch tubes 581, which are used for transporting the front sheath liquid and washing liquid to the front cell 17, respectively. For example, the front sheath liquid may be transported to the front cell 17 through the front sheath liquid inlet 9, and washing liquid may be transported to the front cell 17 through the front cell washing inlet 11. The two first branch tubes 581 may have a front sheath controller 42 and a front cell washing controller 41, respectively, disposed thereon.

The rear sheath liquid adding tube 57 may include two second branch tubes 571 for transporting the rear sheath liquid and washing liquid to the rear sheath isolation chamber 20, respectively. The two second branch tubes 571 may have a rear sheath controller 43 and a rear cell washing controller 45 used for controlling whether the tubes are on or off, respectively. In addition, in the second branch tubes 571 having the rear sheath controller 43, a throttle pipe 44 may also be applied.

When the rear cell needs to be washed, the rear cell washing controller 45 is turned on and the rear sheath controller 43 is turned off, and the washing liquid of the first container 33 flows into the rear cell 18 through the rear sheath isolation chamber 20 and the rear sheath liquid inlet 13. When adding the rear sheath liquid, the rear sheath controller 43 is turned on and the rear cell washing controller 45 is turned off. The rear sheath liquid of the first container 33 flows into the rear cell 18 through the rear sheath isolation chamber 20 and the rear sheath liquid inlet 13. When washing the front cell, the front cell washing controller 41 is turned on and the front sheath controller 42 is turned off. The washing liquid of the first container 33 flows into the front cell 17 through the front cell washing inlet 11. When adding the front sheath liquid, the front sheath controller 42 is turned on and the front cell washing controller 41 is turned off, and the front sheath liquid of the first container 33 flows into the front cell 17 through the front sheath liquid inlet 9.

During a process of discharging the waste liquid isolation chamber 21, because the gas tube 54 is between the waste liquid isolation chamber 21 and the atmosphere, a pressure difference will be formed when gases blow through the gas tube 54; that is, the pressure of the waste liquid isolation chamber 21 is not equal to zero.

In one embodiment, after the discharging process is completed, because there is no air flowing between the waste liquid isolation chamber 21 and the atmosphere, the waste liquid isolation chamber 21 has a pressure of zero. The pressure fluctuation before and after the discharging process influences the liquid surface of the rear sheath isolation chamber 20. In order to eliminate or diminish the influence, a pressure balance tube 59 is provided between the waste liquid isolation chamber 21 and the rear sheath isolation chamber 20. A pressure balance controller 46 may be provided in the pressure balance tube 59. When discharging the waste liquid isolation chamber 21, the pressure balance controller 46 is turned on to keep the waste liquid isolation chamber 21 and the rear sheath isolation chamber 20 in communication with a common pressure.

In order to ensure the sealing of the rear sheath isolation chamber 20 as well as to avoid having bubbles enter into the rear cell 18 from the rear sheath isolation chamber 20 (that is, the rear sheath isolation chamber 20 should not be too full or too empty), the liquid should be stabilized.

In a process of counting and washing, the pressure balance controller 46 is turned off to ensure the rear sheath isolation chamber 20 has the liquid therein with a sealed space 64. In this case, no matter how much liquid flows in, there is the same volume of liquid flowing out. Thus, the liquid surface remains stable.

When washing the rear cell, liquid being added into the rear sheath isolation chamber 20 through the rear cell washing controller 45 has a faster adding speed, and air might be brought into the liquid. If the air further enters into the rear sheath isolation chamber 20, the liquid surface might rise. To solve this problem, the rear sheath isolation 20 may have an oblique guiding surface 60. In one embodiment, the rear sheath isolation chamber 20 includes a first cell body 49 and a first top cover 47 to seal the first cell body 49. The first cell body 49 has a bottom part connected to the rear sheath liquid inlet 13. The first top cover 47 has a first liquid adding inlet 48 and a first connector 61. A bottom of the first liquid adding inlet 48 and a bottom of the first connector 61 both extend downwardly into the first cell body 49. In one embodiment, the first liquid adding inlet 48 is obliquely disposed. Liquid flows in a certain angle to the first side surface 62 of the first cell body 49 and then along the side surface 62 of the first cell body 49, such that the air brought into the liquid during the liquid adding process can be reduced as much as possible.

In some embodiments, the waste liquid isolation chamber 21 includes a second cell body 53 and a second top cover 51 to seal the second cell body 53. A bottom of the second cell body 53 is connected to the second container 36 via the rear sheath waste liquid discharging tube 55. The second top cover 51 has a second liquid adding inlet 52 and a second connector 63. A bottom of the second liquid adding inlet 52 and a bottom of the second connector 63 both extend downwardly into the second cell body 53. The second liquid adding inlet 52 is connected to the waste outlet 14 via a tube. The second connector 63 and the first connector 61 are connected through the pressure balance tube 59.

In order to prevent changes in the liquid surface of the rear sheath isolation chamber 20 due to pressure fluctuations, the counter assembly may periodically undergo a liquid surface initialization.

In order to ensure the initialization is valid, a siphoning process may be used. In one embodiment, the second liquid adding inlet 52 has a bottom with the same height as a predetermined height 50. The bottom of the second liquid adding inlet 52 is lower than the bottom of the first liquid adding inlet 48. During the initialization process, the pressure balance controller 46 is turned on, and the waste liquid isolation chamber 21 and the rear sheath isolation chamber 20 have a common pressure. Excessive liquid is added to the rear sheath isolation chamber 20. When the liquid surface is over the predetermined height 50, the liquid flows from the bottom of the rear sheath isolation chamber 20 and into the waste liquid isolation chamber 21 through the counter 28 and the second liquid adding inlet 52 of the waste liquid isolation chamber 21. This ensures that the initial liquid surface stays at the predetermined height 50.

The counter assembly may further include a shielding box 38. The rear sheath isolation chamber 20, the waste liquid isolation chamber 21, and the counter 28 may be disposed inside the shielding box 38. The controllers 34, 35, 41, 42, 43, 44, 45, and 46 are disposed outside of the shielding box 38. Tubes having liquid flowing therein, such as the front sheath liquid adding tube 58, the rear sheath liquid adding tube 57, the front sheath waste liquid discharging tube 56, and the rear sheath liquid waste discharging tube 55, may have an internal tube portion inside the shielding box 38 and an external tube portion outside the shielding box 38. The internal tube portion and the external tube portion are connected through a shielding connector 23. In addition, the tube connecting the sample liquid inlet 10 may have a shielding connector 23 disposed therein.

In one embodiment, the sheath liquid and the washing liquid can be provided by one container (i.e., the first container) or by different containers. For example, the sheath liquid may be provided by an appropriate sheath liquid container, while the washing liquid may be provided by an appropriate washing liquid container. In one embodiment, the front sheath liquid, rear sheath liquid, front cell cleaner, and rear cell cleaner may be provided by different containers.

The waste liquid of the front cell and the rear cell may be stored in the same container (i.e., the second container) or in different containers. The rear sheath liquid adding tube and the front sheath liquid adding tube may both have one part or a few parts, and the front sheath liquid adding tube and the rear sheath liquid adding tube may be independent from each other or share one or more parts. The controller may be a control valve, such as an electromagnetic valve or a pneumatic pilot valve, or other equipment that can control the tube in order to place it in an on or off state. The guiding surface of the rear sheath isolation chamber may be provided by the first liquid adding inlet, by the first side surface, or by other structures that are able to avoid a direct flow impact.

The sheath flow impedance count device described may be applied in flow cytometer analyzers, such as in blood cell analyzers. However, skilled artisans will recognize that the principles disclosed herein may be used in other types of particle analyzers.

Although the present disclosure has been described with reference to specific embodiments, such embodiments are not intended to limit the invention. Those of skill in the art can make routine modifications without departing from the spirit and scope of the invention.

What is claimed is:

1. A counter assembly comprising a counter, a waste liquid isolation chamber, a rear sheath isolation chamber, and a pressure balance tube; wherein
    the counter has a front cell, a rear cell, a rear sheath liquid inlet, and a waste liquid outlet;
    the front cell and rear cell are in communication through a counting hole;
    the rear sheath liquid inlet and the waste liquid outlet are in communication with the rear cell;
    the rear sheath isolation chamber and the rear sheath liquid inlet are connected with each other;
    the waste liquid isolation chamber is connected with the waste liquid outlet;
    the pressure balance tube is connected with the rear sheath isolation chamber and the waste liquid isolation chamber; and
    the pressure balance tube has a pressure balance controller.

2. The counter assembly according to claim 1, wherein
    the rear sheath isolation chamber comprises a first cell body and a first liquid adding inlet, the first liquid adding inlet extending downwardly into the first cell body;
    the waste liquid isolation chamber comprises a second cell body and a second liquid adding inlet, the second liquid adding inlet extending downwardly into the second cell body; and
    a bottom of the first liquid adding inlet is higher than a bottom of the second liquid adding inlet, and a bottom of the first cell body is higher than a bottom of the second cell body.

3. The counter assembly according to claim 2, wherein the rear sheath isolation chamber further comprises a first top cover disposed at the top of the first cell body, the first liquid adding inlet being disposed at the first top cover, and the first top cover having a first connector;
    wherein the waste liquid isolation chamber further comprises a second top cover disposed at the top of the second cell body, the second liquid adding inlet being disposed at the second top cover, the second top cover having a second connector; and
    wherein the bottom of the first cell body is connected with the rear sheath liquid inlet, and the pressure balance tube is connected with the first connector and the second connector.

4. The counter assembly according to claim 1, wherein the rear sheath isolation chamber is in communication with the atmosphere via a gas tube.

5. The counter assembly according to claim 1, wherein the rear sheath isolation chamber has an oblique guiding surface.

6. The counter assembly according to claim 5, wherein the first liquid adding inlet is disposed obliquely and the guiding surface is a side surface of the first liquid adding inlet.

7. A sheath flow impedance count device comprising:
    a counter assembly comprising a counter, a waste liquid isolation chamber, a rear sheath isolation chamber, and a pressure balance tube; wherein
        the counter has a front cell, a rear cell, a rear sheath liquid inlet, and a waste liquid outlet;
        the front cell and rear cell are in communication through a counting hole;
        the rear sheath liquid inlet and the waste liquid outlet are in communication with the rear cell;
        the rear sheath isolation chamber and the rear sheath liquid inlet are connected with each other;
        the waste liquid isolation chamber is connected with the waste liquid outlet;
        the pressure balance tube is connected with the rear sheath isolation chamber and the waste liquid isolation chamber; and
        the pressure balance tube has a pressure balance controller; and
    a rear sheath adding tube, a front sheath adding tube, a rear sheath waste liquid discharging tube, and a front sheath waste liquid discharging tube, the front sheath adding tube and the front sheath waste liquid discharging tube being connected to the front cell of the counter assembly, the rear sheath isolation chamber being connected to the rear sheath adding tube and the rear cell of the counter assembly, and the rear sheath waste liquid discharging tube being connected to the rear cell of the counter assembly.

8. The device according to claim 7, further comprising a first container and a second container, wherein the front sheath adding tube and the rear sheath adding tube are connected to the first container, and the front sheath waste liquid discharging tube and the rear sheath waste liquid discharging tube are connected to the second container, the first container having a positive pressure, and the second container having a negative pressure.

9. The device according to claim 8, further comprising a shielding box, wherein the counter assembly is located inside of the shielding box; at least one of the rear sheath adding tube, the front sheath adding tube, the rear sheath waste liquid discharging tube, and the front sheath waste liquid discharging tube has an internal tube inside of the shielding box and an external tube outside of the shielding box; and the internal tube and the external tube are connected with each other through a shielding connector.

10. A flow cytometer analyzer comprising:
a counter assembly comprising a counter, a waste liquid isolation chamber, a rear sheath isolation chamber, and a pressure balance tube; wherein
the counter has a front cell, a rear cell, a rear sheath liquid inlet, and a waste liquid outlet;
the front cell and rear cell are in communication through a counting hole;
the rear sheath liquid inlet and the waste liquid outlet are in communication with the rear cell;
the rear sheath isolation chamber and the rear sheath liquid inlet are connected with each other;
the waste liquid isolation chamber is connected with the waste liquid outlet;
the pressure balance tube is connected with the rear sheath isolation chamber and the waste liquid isolation chamber; and
the pressure balance tube has a pressure balance controller.

* * * * *